United States Patent [19]

Prager et al.

[11] Patent Number: 4,562,253
[45] Date of Patent: Dec. 31, 1985

[54] DEACYLATION OF AMIDES

[75] Inventors: Bernhard C. Prager, Kundl; Peter Punk, Breitenbach; Heinrich Thaler, Kirchbichl, all of Austria

[73] Assignee: Biochemie Gesellschaft m.b.H., Tyrol, Austria

[21] Appl. No.: 519,830

[22] Filed: Aug. 3, 1983

[30] Foreign Application Priority Data

Aug. 6, 1982 [AT] Austria ................................. 3024/82

[51] Int. Cl.$^4$ ................... C07D 499/04; C07D 501/04
[52] U.S. Cl. ............................... 544/19; 260/245.2 R; 544/26; 544/27; 544/21
[58] Field of Search ............................ 544/26, 27, 19; 260/245.2 R; 424/246

[56] References Cited

U.S. PATENT DOCUMENTS 4,252,973  2/1981  Slusarchyk et al. ................... 544/27
4,267,321  5/1981  Ascher ................................. 544/030

FOREIGN PATENT DOCUMENTS 280475   4/1970  Austria .
301754   9/1972  Austria .
2258079  6/1973  Fed. Rep. of Germany .
1041985  9/1966  United Kingdom .
1119806  7/1968  United Kingdom .
1239814  7/1971  United Kingdom .
1241655  8/1971  United Kingdom .
1270448  4/1972  United Kingdom .

OTHER PUBLICATIONS

L. Ander, J. Chem. Soc. 83 320(1903).

Primary Examiner—Nicholas S. Rizzo
Attorney, Agent, or Firm—Gerald D. Sharkin; Richard E. Vila; Frederick H. Weinfeldt

[57] ABSTRACT

De-acylation of Penicillins and Cephalosporins to obtain the corresponding 6-aminopenicillanic acid or 7-aminocephalosporanic acid by the imino halide/imino ether process using long chain bases.

11 Claims, No Drawings

DEACYLATION OF AMIDES

This invention relates to the removal of the acyl group (deacylation) of amides to obtain the corresponding amines. More particularly, the present invention relates to the deacylation of penicillins and cephalosporins to obtain the corresponding 6-amino-penicillanic acid or 7-aminocephalosporanic acid.

It is known to deacylate amides by the so-called iminohalide/iminoether process, in which the amide is treated with a halogenating agent to form the corresponding iminohalide, which is then converted to the corresponding iminoether by treatment with an alcohol. The iminoether is then hydrolysed or alcoholysed to obtain the corresponding amino and ester. This reaction sequence is described for example in Lander, J. Chem. Soc. 83, 320 (1903) and in W. German DOS No. 2,258,079.

Numerous publications, for example B. Fechtig et al, Helv. Chim. Acta 51, 1108 (1968) and R. R. Chauvette et al, J. Org. Chem. 36, 1259 (1971) as well as patent specifications, for example Austrian Pat. Nos. 280,475 and 301,754, and U.S. Pat. Nos. 3,234,223; 3,575,970 and 3,549,628 describe the application of the iminohalide/iminoether process to the deacylation of penicillins and cephalosporins. The products resulting are the key penicillin and cephalosporin basic structures such as 6-aminopenicillanic acid (6-APA), 7-aminocephalosporin acid (7-ACA), 7-aminodesacetoxycephalosporanic acid (7-ADCA) and derivatives thereof, such as esters or salts. The iminohalide/iminoether process is in worldwide technical use for the commercial production of such penicillin and cephalosporin intermediates.

In all of these processes, the treatment with a halogenating agent, such as phosphorus pentachloride, to form the iminohalide (the iminochloride in the case of treatment with $PCl_5$) is effected in the presence of a base as acid binding agent. The most commonly employed bases, such as pyridine, dimethylaniline and diethylaniline are, however, questionable from the ecological point of view, and are very difficult to remove as impurities in the final products in which they may therefore be present in quantities of up to 1000 p.p.m. or more. The regeneration or complete removal of these bases from the mother liquor or waste water is also very difficult, time consuming and expensive.

The present invention relates to the use, in the iminohalide formation step, of bases which are acceptable from the ecological viewpoint, can easily be regenerated and whose presence as impurity in the final products can be substantially or completely eliminated.

More particularly, the present invention provides a process for the deacylation of an amide to form a corresponding amine, by treatment of the amide with a halogenating agent in the presence of a base to form a corresponding iminohalide, conversion of this into an iminoether by treatment with an alcohol, and hydrolysis or alcoholysis or the resulting iminoether, characterised in that a long-chain substituted aromatic amine, a long-chain substituted pyridine, or a polymer-bound pyridine is employed as base.

Preferred long chain substituted aromatic amines include those of formula IX,

in which $R_{11}$ and $R_{12}$ are the same or different and each signify hydrogen, halogen, trihalomethyl, nitro, lower alkyl, or lower alkoxy, $R_{13}$ signifies a $C_{1-18}$ straight chain or branched alkyl group and $R_{14}$ signifies a $C_{8-18}$ straight chain or branched alkyl group.

Preferred compounds of formula IX include N-methyl-N-decylaniline, N-methyl-N-dodecylaniline, N-ethyl-N-decylaniline, N-ethyl-N-dodecylaniline, N-methyl-N-tetradecylaniline, N-methyl-N-hexadecylaniline, N-methyl-N-octadecylaniline, N,N-dioctylaniline, N-methyl-N-dodeyl-o-toluidine, N-methyl-N-dodecyl-p-anisidine and N-methyl-N-hexadecyl-p-anisidine.

Other preferred long-chain substituted aromatic amines are those of formula X

in which $R_{14}$ is as defined above, and $R_{15}$ and $R_{16}$ are the same or different and signify $C_{1-4}$ alkyl.

The preferred compounds of formula X include dodecyl-p-(N,N-dimethylamino)phenylether and hexadecyl-p-(N,N-dimethylamino)phenylether.

The preferred long-chain substituted pyridines include those of formula XI

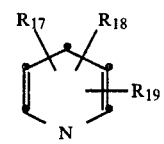

in which $R_{17}$ signifies straight or branched chain $C_{6-20}$ alkyl, and $R_{18}$ and $R_{19}$ are the same or different and signify hydrogen or straight or branched $C_{1-18}$ alkyl.

Preferred compounds of formula XI include 2-dodecylpyridine, 3-dodecylpyridine, 4-dodecylpyridine, 2-octadecylpyridine, 2,6-dinonylpyridine, 2,6-dimethyl-4-hexylpyridine, 2,6-dimethyl-4-tridecylpyridine and 2,6-dimethyl-4-pentadecylpyridine.

Preferred polymer-bound pyridines include those containing a repeating unit of formula XII,

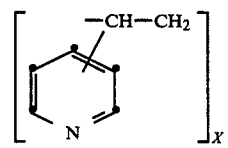

for example the polyvinylpyridine available from Reilly Tar and Chemical Corporation.

The bases employed on the process of the invention are suitably used in at least equimolar quantities based on the halogenating agent. They may be removed, in the form eg of their salts formed in the reaction mixture by extraction with an organic, water-immiscible solvent, or in the case polymer-bound pyridine, by filtration, prior to isolation of the end product.

Whereas the bases hitherto employed in the iminohalide/iminoether process are not extractable from the aqueous/alcoholic phase resulting after the hydrolysis/alcoholysis step, the bases used in accordance with the present invention may be extracted at any desired pH value in salt or free base form easily and substantially completely, as indicated either by extraction with an organic water-immiscible solvent, or by filtration. As a result, the quantity of trace base remaining in the final product may be reduced to less than 10 ppm whereas with hitherto employed bases quantities of less than 200 to 1000 ppm could only be achieved with difficulty. In addition, the bases employed in the present invention can, without difficulty, be regenerated more or less quantitatively. On the basis of their marked by hydrophobicity, these bases (in free base form or in salt form) or substantially insoluble in water and lower alcohols (as used for example in the iminoether formation step) whereas they are easily soluble in most water-immiscible organic solvents, for example methylene dichloride. The organic extract may then simply be washed with acid and then alkali and evaporated to regenerate the base for further use in the process.

The individual steps of the process may be carried out in the same manner as described in the literature. In particular, the iminohalide, desirably the iminochloride, may be formed by treatment with for example phosphorus pentachloride, suitably in an organic solvent such as methylene dichloride, desirably at a reduced temperature. The subsequent formation of the iminoether may for example be accomplished with lower alkanol such as methanol, again desirably at a reduced temperature and preferably in the presence of a base, suitably the same base employed in the iminohalide formation step. The iminoether may then be hydrolysed with water or alcoholysed with for example a lower alkanol, for example methanol, for example in the presence of a basic or acidic catelyst.

As is conventional, it may be desirable in the process of the invention to protect any reactive groups, for example carboxylic acid groups or free amino groups in the starting material, prior to the iminohalide formation step, and to remove such protecting groups after completion of the process if they have not already been removed simultaneously during the hydrolysis/alcoholysis step.

The process of the invention has particular applicability to the deacylation of penicillins and cephalosporins and derivatives thereof. More particularly, the present invention a process for the production of compounds of formula I,

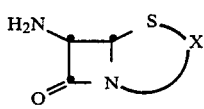
(I)

in which X is a group of formula II or IIa,

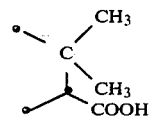
(II)

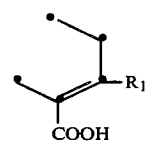
(IIa)

in which $R_1$ is methyl, methoxy, halogen, acetoxymethyl or $-CH_2-S-$heterocyclic, and esters and salts thereof,
comprising deacylating a compound of formula III

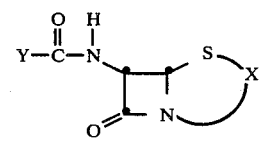
(III)

in which

X is defined above, and Y—CO— is a carboxylic acid acyl group,
and esters or salts thereof, by the process of the invention.

The carboxylic acid acyl group Y—CO— may be any acyl group present in natural, semi-synthetic or synthetic penicillins and cephalosporins. The preferred groups are those in which:

Y is hydrogen, $C_{1-6}$ alkyl optionally substituted one or more times by halogen, or a group of formula IV or VIII, $$R_2O-CO-CH-(CH_2)_3- \atop NHR_3 \qquad (IV)$$

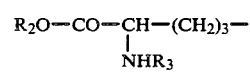
(VIII)

in which $R_2$ is hydrogen, lower alkyl, benzyl or diphenylmethyl, $R_3$ is hydrogen or a group of formula V or VI,

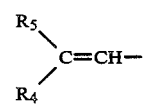
(V)

(VI)

in which $R_4$ and $R_5$ are the same or different and signify hydrogen, nitro, cyano, acyl or lower alkoxycarbonyl, A is O or NH, and $R_6$ is lower alkyl or a group of formula VII,

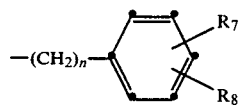

in which
n is 1 to 6 when A is O, and
0 to 6 when A is NH, and
$R_7$ and $R_8$ are the same or different and signify hydrogen, halogen, nitro, lower alkyl or lower alkoxy,
$R_9$ and $R_{10}$ are the same or different and signify hydrogen, halogen, lower alkyl, lower alkoxy, hydroxy, or amino,
Z is oxygen or sulphur, and m is 0 or 1.

Particular penicillins, cephalosporins and derivatives thereof which may be deacylated in accordance with the invention include the following:

Penicillin V, penicillin G, cephalosporin C, 6-chloracetamidopenicillanic acid, N-[2,2-diethoxycarbonylvinyl(1)]cephalosporin C, N-[2-nitro-2-carbethoxyvinyl(1)]cephalosporin C, 7-[N-(2,2-diethoxycarbonyl)vinyl]adipinoylamino-3-[(1-methyl-1,2,3,4-tetrazol-5-yl)thiomethyl]ceph-3-em-4-carboxylic acid, 7-[N-(2,2-diethoxycarbonyl)vinyl]adipinamido-3-[(2,5-dihydro-6-hydroxy-5-oxo-2-methyl-1,2,4-triazin-3-yl)thiomethyl]ceph-3-em-4-carboxylic acid, 7-[N-(2,2-diethoxycarbonyl)vinyl]adipinamido-3-[(4,5-dihydro-6-hydroxy-5-oxo-4-methyl-1,2,4-triazin-3-yl)thiomethyl]-ceph-3-em-4-carboxylic acid, 3-desacetoxy-3-(1-methyl-1,2,3,4-tetrazol-5-yl)thiocephalosporin C, 3-desacetoxy-3-(2,5-dihydro-6-hydroxy-5-oxo-2-methyl-1,2,4-triazin-3-yl)thiocephalosporin C, 3-desacetoxy-3-(4,5-dihydro-6-hydroxy-5-oxo-4-methyl-1,2,4-triazin-3-yl)thiocephalosporin C, 7-phenoxyacetamido-3-methylceph-3-em-4-carboxylic acid, 7-chloracetamido-3-methylceph-3-em-4-carboxylic acid, 7-phenylacetamido-3-methylceph-3-em-4-carboxylic acid, N-ethoxycarbonylcephalosporin C, N-methoxycarbonylcephalosporin C, N-iso-butoxycarbonylcephalosporin C, N-iso-propyloxycarbonylcephalosporin C, N-(N'-butylcarbamoyl)cephalosporin C, N-(N'-phenylcarbamoyl)cephalosporin C, N-chloracetylcephalosporin C, and 7-benzylamino-3-methylceph-3-em-4-carboxylic acid.

When the starting materials of formula III contain reactive groups, these may, as indicated, desirably be protected during the reaction. In particular, where the starting material is in free carboxylic acid form, this is desirably protected by esterification, preferably by silylation, eg with trimethylchlorosilane. The trimethylsilyl group is then cleaved during the subsequent hydrolysis-/alcoholysis step. The deacylated end products of formula I may conveniently be isolated from the reaction mixture by adjustment of the pH thereof to isolectric point and desirably the base employed is, as described above, removed prior to this stage.

The bases employed in accordance with the invention are known or may be prepared in known manner from available starting materials. See, for example, Tanaka et al, J.Pharm.Soc.Jap. 63, 353 (1943), DT-PS 611, 283 (1933), Krafft and Mai, Berichte 22, 1758, Urry and Juveland, J.Am.Chem.Soc., 80, 3322, 3327 (1958), Wibaut and Hoogzand, Chem.Weekb. 52, 357, Ames and Bowman, J.Chem.Soc. 1952, 1057 and 1063, Knight and Shaw, J.Chem.Soc., 1938, 682, Tschitschibabin, Chem.-Zentr. 1906(1), 1439, Gottfried and Ulzer, Chem.Zentr. 1928(1), 1193, Wibaut and Hey, Rec.Trav.Chim. 72, 513, 520 (1953) and Barkovsky, Ann.Chim. (11) 19, 487, 502 (1944).

The following examples illustrate the invention. All degrees are in Centigrade.

EXAMPLE 1

7-Aminocephalosporanic acid (7-ACA)

58.5 g of N-(2,2-diethoxycarbonyl)vinylcephalosporin C are suspended in 500 ml of methylene dichloride under an inert gas atmosphere. After addition of 65 ml of trimethylchlorosilane, 10 g of ammonia gas are quickly introduced under the liquid surface level whereupon the temperature rises. The mixture is boiled for 10 minutes and then cooled to $-14°$. 70 g of N-methyl-N-dodecylaniline are added and the mixture is again cooled to $-14°$. Under continuous cooling, 35 g of phosporus pentachloride are added over the course of 30 minutes, the temperature being held at $-12°$ to $-8°$. After 20 minutes stirring at about $-10°$, the reaction mixture is poured into 500 ml of dried, cooled to $-12°$, methanol. The resulting mixture is stirred into 500 ml of ice water, the phases are separated, and the aqueous phase is extracted with a 100 ml of methylene dichloride. The pH value of the aqueous phase is adjusted to 3.5 by addition of ammonia solution over 15 minutes. The mixture is stirred for 15 minutes and the precipitate is collected on a glass frit, washed with 50 ml of water and acetone and dried in vacuo at 50°. 23.7 g (87% of theory) of pure, colourless 7-ACA is obtained. To regenerate the N-methyl-N-dodecylaniline employed, the organic phase is washed with 2N HCl, 2N NaOH, and water. The methylene/dichloride and hexamethyldisiloxan are distilled of at normal pressure. N-Methyl-N-dodecylaniline remains as residue (97% of regeneration yield).

EXAMPLE 2

7-Aminocephalosporanic acid 47,3 g of cephalosporin C sodium salt dihydrate are silylated as in Example 1 with 63 ml of trimethylchlorosilane and 10 g of ammonia and reacted with 35 g of phosphorus pentachloride in the presence of 70 ml of N-methyl-N-dodecylaniline as described in Example 1. After alcoholysis and hydrolysis, phase separation and pH adjustment in the same manner as in Example 1, 24.2 g (89%) of pure 7-ACA are obtained.

EXAMPLE 3

7-Amino-3-(1-methyl-1,2,3,4-tetrazol-5-yl)thiomethyl-ceph-3-em-4-carboxylic acid 6.3 g of 7-[N-(2,2-diethoxycarbonyl)vinyl]adipinamido-3-[(1-methyl-1,2,3,4-tetrazol-5-yl)thiomethyl]ceph-3-em-4-carboxylic acid are suspended in 50 ml of dried methylene dichloride and mixed with 18 ml of N-ethyl-N-dodecylaniline. 4.8 ml of trimethylchlorsilane are added dropwise and the mixture is stirred for 15 minutes at about 30°. After cooling to $-12°$, 3.75 g of phosphorus pentachloride are added and the reaction mixture is stirred for a further 40 minutes at about $-10°$. The mixture is then poured into 80 ml of dried methanol, pre-cooled to $-14°$. After addition of 80 ml of ice water, the mixture is stirred for a further 3 minutes and the phases are separated. The aqueous phase is extracted with 30 ml of methylene dichloride and the pH is adjusted to 3.5 with ammonia solution. The mixture is stirred for 15 minutes and the precipitate is filtered off, washed with 30 ml each of water and acetone and dried at 50° in vacuo. 2.7 g (82%) of the pure title compound results. The N-ethyl-N-dodecylaniline base can be regenerated as described in Example 1 for N-methyl-N-dodecylaniline.

EXAMPLE 4

6-Aminopenicillanic acid (6-APA)

11.64 g of phenoxymethylpenicillanic acid potassium salt are suspended in 120 ml of dried methylene dichloride. 7.6 ml of trimethylchlorosilane are added and ammonia gas is introduced until the temperature which has arisen to about 35° begins to drop. Nitrogen is blown into the reaction mixture for 10 minutes and the mixture is then cooled to −20°. 13.8 ml of N-methyl-N-tetradecylaniline are added and the mixture is cooled again to −20°. 8.9 g of phosphorus pentachloride are added in 3 portions so that the temperature does not rise above −18°. After stirring for a further 20 minutes at −20°, the mixture is cooled to −30° and poured into 150 ml of methanol, pre-cooled to −40°. The resulting mixture is poured into 150 ml of ice water, stirred for 3 minutes, then the phases are separated. The aqueous phase is extracted with 30 ml of methylene dichloride and the pH value is adjusted to 4.2 with ammonia solution. The colourless precipitate is filtered off, washed with 30 ml of water and 30 ml of acetone and dried at 40° in vacuo. 5.56 g (86%) of pure heading compound in the form of a colourless powder is obtained. The N-methyl-N-tetradecylaniline base can be regenerated in the same manner as described in Example 1 for N-methyl-N-dodecylaniline.

EXAMPLE 5

7-Amino-3-methyl-3-cephem-4-carboxylic acid (7-ADCA)

8.7 g of 7-chloroacetylamino-3-methyl-3-cephem-4-carboxylic acid are suspended in a 100 ml of methylene dichloride and 7.4 ml of trimethylchlorosilane are added. Dry ammonia gas is then introduced until the temperature which has arisen begins to sink. After refluxing for a short time and cooling to −14°, 15.8 ml of N-ethyl-N-hexadecylaniline are added. 8 g of phosphorus pentachloride are then added in 3 portions so that the temperature does not rise above −10°. The reaction mixture is stirred for a further 30 minutes at −12° to −10° and then poured into 150 ml of methanol, pre-cooled to −14°. The mixture is then mixed with 150 ml of ice water. After strong stirring for a short time, the phases are separated. The aqueous phase is washed with methylene dichloride and the pH is adjusted to 3.8 with ammonia solution. The colourless precipitate is filtered off, washed each time with 30 ml of water and acetone and dried in vacuo at 50°. The title compound (5.85 g; 91%) results as a colourless powder in pure form. The N-ethyl-N-hexadecylaniline base can be regenerated in the same manner as described in Example 1 for N-methyl-N-dodecylaniline.

EXAMPLE 6

7-Amino-3-(2,5-dihydro-6-hydroxy-5-oxo-2-methyl-1,2,4-triazin-3-yl)thiomethyl-3-cephem-4-carboxylic acid 14 g of 7-[N-(2,2-diethoxycarbonyl)vinyl]adipinoylamino-3-(2,5-dihydro-6-hydroxy-5-oxo-2-methyl-1,2,4-triazin-3-yl)thiomethyl-3-cephem-4-carboxylic acid are suspended in 80 ml of methylene dichloride. 40 ml of N-methyl-N-dodecylaniline are added, followed by dropwise addition of 12 ml of trimethylchlorosilane, whereupon the temperature rises. The mixture is stirred at 35° for 10 minutes and then cooled to −14°. 9.15 g of phosphorus pentachloride are introduced, the temperature being maintained below −10°, and the mixture is stirred at −12° for 35 minutes. The mixture is then poured into 120 ml of methanol, cooled to −14°. The resulting mixture is poured into 150 ml of ice water, and stirred well for 3 minutes. The phases are separated and the aqueous phase is washed with 30 ml of methylene dichloride. The pH value of the aqueous phase is adjusted to 3 with ammonia solution and the colourless precipitate is filtered off, washed with 30 ml of water, 30 ml of methanol and 30 ml of acetone and dried at 40° in vacuo. 6.07 g (82%) of pure title compound results.

EXAMPLE 7

7-Aminodesacetoxycephalosporanic acid (7-ADCA)

33.2 g of 7-phenylacetylaminodesacetoxycephalosporanic acid are suspended in 300 ml of methylene dichloride and 16 g of trimethylchlorsilane are added. Dry ammonia is then introduced, whereupon the internal temperature rises to approximately 35°. After the exothermic reaction has ended, the ammonia introduction is stopped and the mixture is refluxed for 10 minutes. The mixture is cooled in the absence of moisture to −14° and 38.1 g of 2,6-dimethyl-4-pentadecylpyridine are added. 22 g of phosphorus pentachloride are added portionwise under cooling, care being taken that the internal temperature does not rise above −5°. After stirring for 1 hour at −10° to −5°, the reaction mixture is poured into 100 ml of methanol, pre-cooled to −14° and thereafter hydrolysed with 250 ml of ice water. The phases are separated and the aqueous phase is extracted with 50 ml of methylene dichloride. The 7-ADCA is precipitated from the aqueous phase by adjustment of the pH value to 3.8 to 4 with ammonia solution, and is filtered off, washed with water and methanol and dried in vacuo at 50°. 19.1 g (89%) of pure 7-ADCA results.

The base employed may be regenerated in the same manner as described in Example 1.

EXAMPLE 8

7-Aminocephalosporanic acid 29.25 g of N-(2,2-diethoxycarbonylvinyl)cephalosporin C and 28 g of polyvinylpyridine are suspended in 300 ml of methylene dichloride and 38 g of trimethylchlorosilane are added. Dry ammonia is introduced whereupon the temperature rises to about 39° to 40°. As soon as the temperature begins to drop again the ammonia introduction is ceased and the mixture is cooled under nitrogen to −14°. At this temperature, 20.8 g of phosphorus pentachloride are added the temperature being maintained under −5°. After stirring for 1 hour at about −10°, the reaction mixture is poured into 100 ml of methanol, pre-cooled to −14° and this mixture is then hydrolysed with 250 ml of ice water. The polyvinylpyridine hydrochloride is separated from the resulting 2-phase mixture by filtration and the phases are then separated. The 7-ACA is precipitated from the aqueous phase by adjustment of the pH value with ammonia to 3.5 and is collected on a glass frit, washed with water and methanol and dried at 50° in vacuo. 11.6 g (86%) of pure title compound results.

The polyvinylpyridine hydrochloride is regenerated by stirring with 2N NaOH followed by washing neutral with water and drying in vacuo at 100°.

What is claimed is:

1. In an iminohalide/iminoether reaction for converting amido groups to amino groups present on a penicillin or cephalosporin selected from the group consisting of penicillin V, penicillin G, cephalosporin C, 6-chloracetamidopenicillanic acid, N-[2,2-diethoxycarbonylvinyl(1)]cephalosporin C, N-[2-nitro-2-carbethoxyvinyl(1)]cephalosporin C, 7-[N-(2,2-diethoxycarbonyl)vinyl]adipinoylamino-3-[(1-methyl-1,2,3,4-tetrazol-5-yl)thiomethyl]ceph-3-em-4-carboxylic acid, 7-[N-(2,2-diethoxycarbonyl)vinyl]adipinamido-3-[(2,5-dihydro-6-hydroxy-5-oxo-2-methyl-1,2,4-triazin-3-yl)thiomethyl]ceph-3-em-4-carboxylic acid, 7-[N-(2,2-diethoxycarbonyl)vinyl]adipinamido-3-[(4,5-dihydro-6-hydroxy-5-oxo-4-methyl-1,2,4-triazin-3-yl)thiomethyl]-ceph-3-em-4-carboxylic acid, 3-desacetoxy-3-(1-methyl-1,2,3,4-tetrazol-5-yl)thiocephalosporin C, 3-desacetoxy-3-(2,5-dihydro-6-hydroxy-5-oxo-2-methyl-1,2,4-triazin-3-yl)thiocephalosporin C, 3-desacetoxy-3-(4,5-dihydro-6-hydroxy-5-oxo-4-methyl-1,2,4-triazin-3-yl)thiocephalosporin C, 7-phenoxyacetamido-3-methylceph-3-em-4-carboxylic acid, 7-chloracetamido-3-methylceph-3-em-4-carboxylic acid, 7-phenylacetamido-3-methylceph-3-em-4-carboxylic acid, N-ethoxycarbonylcephalosporin C, N-methoxycarbonylcephalosporin C, N-isobutoxycarbonylcephalosporin C, N-iso-propyloxycarbonylcephalosporin C, N-(N'-butylcarbamoyl)-cephalosporin C, N-(N'-phenylcarbamoyl)cephalosporin C, N-chloracetylcephalosporin C, or 7-benzylamino-3-methylceph-3-em-4-carboxylic acid; to prepare an amino-compound of formula I,

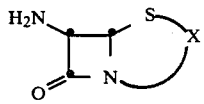

in which X is a group of formula II or IIa,

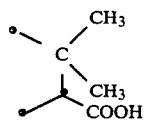

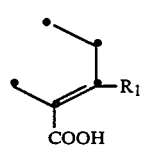

in which
$R_1$ is methyl, methoxy, halogen, acetoxymethyl or —$CH_2$—S-heterocyclic, and esters and salts thereof,
comprising deacylating said penicillin or cephalosporin of formula III

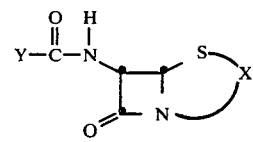

in which
X is defined above, and
Y—CO— is a carboxylic acid acyl group, or an ester or salt thereof; the improvement comprising treating said penicillin or cephalosporin with a halogenating agent in the presence of a base to form a corresponding iminohalide; wherein said base is selected from the group consisting of:

(A) long chain substituted aromatic amines of formula IX,

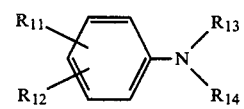

in which $R_{11}$ and $R_{12}$ are the same or different and each signify hydrogen, halogen, trihalomethyl, nitro, lower alkyl or lower alkoxy; $R_{13}$ signifies a $C_{1-18}$ alkyl group; and $R_{14}$ signifies a $C_{8-18}$ alkyl group;

(B) long-chain substituted aromatic amines of formula X,

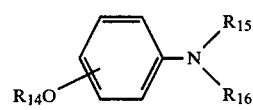

in which $R_{14}$ is as defined above, and $R_{15}$ and $R_{16}$ are the same or different and signify a $C_{1-14}$ alkyl group;

(C) long-chain substituted pyridines of formula XI

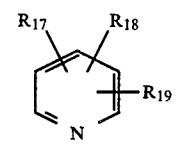

in which $R_{17}$ signifies a $C_{6-20}$ alkyl group, and $R_{18}$ and $R_{19}$ are the same or different and signify hydrogen or a $C_{1-18}$ alkyl group, and (D) polymeric pyridines containing repeating units of units of formula XII,

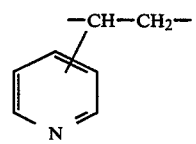

and after the alcoholysis and hydrolysis, essentially removing said base in free base or salt form, from the resulting aqueous mixture by extracting in a water-immiscible organic solvent, or by filtration.

2. A process of claim 1 in which the base is of formula IX, as defined.

3. A process of claim 1 in which the base is of formula X, as defined.

4. A process of claim 1 in which the base is of formula XI, as defined.

5. A process of claim 1 in which the base is of formula XII, as defined.

6. A process of claim 1, in which the base of formula IX is N-methyl-N-decylaniline, N-methyl-N-dodecylaniline, N-ethyl-N-decylaniline, N-ethyl-N-dodecylaniline, N-methyl-N-tetradecylaniline, N-methyl-N-hexadecylaniline, N-methyl-N-octadecylaniline, N,N-dioctylaniline, N-methyl-N-dodecyl-o-toluidine, N-methyl-N-dodecyl-p-anisidine or N-methyl-N-hexadecyl-p-anisidine.

7. A process of claim 1 in which the base of formula X is dodecyl-p-(N,N-dimethylamino)phenyl ether, or hexadecyl-p-(N,N-dimethylamino)phenyl ether.

8. A process of claim 1 in which the base of formula XI is 2-dodecylpyridine, 3-dodecylpyridine, 4-dodecylpyridine, 2-octadecylpridine, 2,6-dinonylpyridine, 2,6-dimethyl-4-hexylpyridine, 2,6-dimethyl-4-tridecylpyridine or 2,6-dimethyl-4-pentadecylpyridine.

9. A process according to claim 1 in which the base employed is used in at least an equimolar quantity based on the halogenating agent.

10. A process according to claim 1 in which the base is removed from the reaction mixture in the form of its salt formed in the reaction mixture, by extraction with an organic, water-immiscible solvent, or where the base is polymer-bound pyridine, by filtration prior to isolation of the end product.

11. A process according to claim 1, whereby an end product is obtained wherein the quantity of base remaining in the end product is less than 10 parts per million of said end product.

* * * * *